United States Patent [19]

Gaertner

[11] 4,105,432

[45] Aug. 8, 1978

[54] CYCLIZED DERIVATIVES OF N-(2-HYDROXYALKYL)-N-PHOSPHONOMETHYLGLYCINE COMPOUNDS

[75] Inventor: Van R. Gaertner, Ballwin, Mo.

[73] Assignee: Monsanto Company, St. Louis, Mo.

[21] Appl. No.: 816,616

[22] Filed: Jul. 18, 1977

[51] Int. Cl.$^2$ ............................ C07F 9/38; A01N 9/36
[52] U.S. Cl. ........................................... 71/86; 544/157
[58] Field of Search ............................ 544/157; 71/86

[56] References Cited

U.S. PATENT DOCUMENTS 2,635,112  4/1953  Fields ................................. 260/945

*Primary Examiner*—Henry R. Jiles
*Assistant Examiner*—R. W. Ramsuer
*Attorney, Agent, or Firm*—Arnold H. Cole; Donald W. Peterson

[57] ABSTRACT

Lactones prepared by cyclizing certain N-(2-hydroxyalkyl)-N-phosphonomethylglycine compounds are useful as post-emergent herbicides for the treatment of undesired plants.

30 Claims, No Drawings

CYCLIZED DERIVATIVES OF N-(2-HYDROXYALKYL)-N-PHOSPHONOMETHYLGLYCINE COMPOUNDS

This invention relates to a new class of chemical compounds which are lactones of N-(2-hydroxyalkyl)-N-phosphonomethylglycines. These new compounds can be employed in herbicidal compositions for the post-emergent treatment of undesired plants.

U.S. Pat. No. 3,799,758 teaches that N-phosphonomethylglycine, and certain esters, amides and salts thereof, are useful as post-emergent herbicides for undesired plants. A very similar class of compounds, including certain N-acyl derivatives, is described in U.S. Pat. No. 3,853,530 as useful for the non-lethal regulation of the natural growth and development of desirable plants. Various other N-substituted derivatives of N-phosphonomethylglycine are also shown to be useful for herbicidal and/or plant growth regulating purposes in U.S. Pat. No. 3,888,915, 3,910,969 and 3,933,946.

In copending applications Ser. No. 714,054, filed Aug. 13, 1976 and Ser. No. 798,043, filed May 18, 1977, there is described a new class of N-(2-hydroxyalkyl) derivatives of N-phosphonomethylglycine. It has now been found that the compounds of said copending applications can be converted to lactones. In accordance with the present invention, such lactones may be represented by the formula

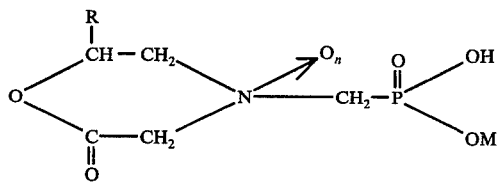

wherein $n$ is zero or one, M is hydrogen or alkali metal, and R is hydrogen, methyl, ethyl, hydroxymethyl, lower alkoxymethyl or lower alkenoxymethyl. As employed herein, lower designates those radicals containing up to four carbon atoms in a straight or branched chain.

The lactones of this invention may be prepared by acidifying the N-(2-hydroxyalkyl) compounds of the aforesaid copending applications. The method of making such starting materials is described both generally and by illustrative examples in said applications. Such method involves the reaction of an epoxide with a salt of N-phosphonomethylglycine under controlled pH conditions. The product of this reaction is a salt which can be acidified to the corresponding acid. However, as noted in said applications, this acidification should be at room temperature or below since the acids are not particularly stable at any elevated temperatures.

Acidification of said starting materials to the lactones of the present invention can be accomplished by contact with a suitable acid, although it is preferred to employ ion exchange chromatography using an ion exchange resin in the acid form. The temperature instability problem of the copending applications is not of concern here since the tendency at elevated temperatures is toward lactonization.

The examples which follow will serve to further illustrate the preparation of certain individual compounds of this invention.

EXAMPLE 1

A solution of N-phosphonomethylglycine (16.9 grams, 0.1 mole) in 30 ml. of water is titrated to a pH of about 9 (phenolphthalein) with 50% aqueous sodium hydroxide (16 grams, 0.2 mole). The solution is cooled at 0°–5° C. in a stainless steel bomb, and ethylene oxide (6.6 grams, 0.15 mole) is added. The bomb is sealed, allowed to warm to room temperature and then heated gradually with shaking. The temperature is held at about 45° C. for 30 minutes, at 60°–65° C. for about 90 minutes, and the bomb is then cooled and vented. The solution is then filtered, concentrated on a rotoevaporator and filtered again. The residue is dissolved in water, acidified with concentrated HCl and precipitated with ethanol. Sodium chloride precipitate is discarded, and the remaining filtrate is rotoevaporated to dryness at 100° C. and redried over potassium hydroxide pellets at 1 mm. The product, obtained as a white foamed glass, is the monosodium salt of 4-phosphonomethyl-2-morpholinone.

EXAMPLE 2

To a slurry of N-phosphonomethylglycine (16.9 grams, 0.1 mole) in 50 ml. of water is added 50% aqueous sodium hydroxide (16 grams, 0.2 mole). The mixture is stirred and cooled to 35° C. in a flask equipped with a pressure-equalized dropping funnel and a dry-ice condenser vented to atmosphere. Propylene oxide (6.0 grams) is added, and the solution is stirred overnight. A further portion of propylene oxide (2.0 grams) is added, and, after stirring, the solution is allowed to stand for several days. It is rotoevaporated to dryness, and the solid is redried in vacuo over pellets of potassium hydroxide to give the disodium salt of N-(2-hydroxy-1-propyl)-N-phosphonomethylglycine. A 7.0 gram portion of this material is acidified to a pH of about 3 with concentrated HCl, rotoevaporated to dryness at <1 mm., and redried over potassium hydroxide pellets in a dessicator. The product is redissolved in 15 ml. of water, and 5 ml. of concentrated HCl is added. After heating for 30 minutes on a steam bath, large crystals form on standing. The liquid is decanted and rotoevaporated to dryness to yield the monosodium salt of 6-methyl-4-phosphonomethyl-2-morpholinone as a white brittle foam.

EXAMPLE 3

A solution of N-phosphonomethylglycine and sodium hydroxide is prepared as in Example 1, and ethylene oxide (5.0 grams, 0.114 mole) is added through a dry-ice condenser. After stirring overnight and standing for several days, successive portions of 0.5 and 1.0 grams of ethylene oxide are added. The solution is rotoevaporated to dryness, and the solid is redried to give the disodium salt of N-(2-hydroxyethyl)-N-phosphonomethylglycine. A 10 gram portion of the product is acidified to pH 1 (pHydrion paper) with concentrated HCl, cooled and treated immediately with 30% hydrogen peroxide (6.8 grams). The solution is heated overnight at 45° C. and concentrated to dryness below 50° C. The residue is redissolved in water, filtered and rotoevaporated again. The colorless gummy solid is dissolved in water and identified by nuclear magnetic resonance as the monosodium salt of 4-phosphonomethyl-2-morpholinone, N-oxide.

EXAMPLE 4

To a solution of N-phosphonomethylglycine (8.5 grams, 0.05 mole) in 30 ml. of water is added 50% aqueous sodium hydroxide (8.0 grams). The solution is cooled, and 1,2-butylene oxide (3.6 grams, 0.05 mole) is added, after which the solution is rotated overnight on a polymer wheel. Additional amounts of 1,2-butylene oxide are added to complete the reaction, and any unreacted butylene oxide is then extracted with ethyl ether and benzene. A portion of the reaction product is diluted with water and passed through a column of ion exchange resin in the acid form. Cuts 3 through 20 are collected, combined and evaporated to dryness to give 6-ethyl-4-phosphonomethyl-2-morpholinone as a friable glassy solid.

EXAMPLE 5

A solution of N-phosphonomethylglycine and sodium hydroxide is prepared as in Example 1, and glycidol (8.1 grams, 0.11 mole) is added. After stirring and warming overnight in a melting ice bath, a further 2.0 grams of glycidol is added. The solution is stirred at 22° C., allowed to stand for several days and rotoevaporated to dryness. The solid obtained is redried over potassium hydroxide to give a glass. A 10 gram portion of this glass is cooled, broken up and dissolved in water. The solution is passed through a column of ion exchange resin in the acid form, and cuts 15 through 18 are collected and vacuum dried at about 100° C. The product, obtained as white crystals, is 6-hydroxymethyl-4-phosphonomethyl-2-morpholinone (in the dihydrate form), m.p. 118°–121° C. (dec.). Elemental analysis gives 28.07% carbon, 5.81% hydrogen, 5.22% nitrogen and 12.09% phosphorus as against calculated values of 27.59%, 6.18%, 5.36% and 11.86% for $C_6H_{12}NO_6P \cdot 2H_2O$.

EXAMPLE 6

The disodium salt of N-(2-hydroxy-1-propyl)-N-phosphonomethylglycine is prepared as described in Example 2, dissolved in water, and passed through a column of ion exchange resin in the acid form. The fractions obtained are combined and heated on a steam bath in 50 ml. of water with 5 ml. of concentrated HCl. The solution is evaporated to dryness and redried over potassium hydroxide pellets. The product, obtained as a colorless friable glass, is 6-methyl-4-phosphonomethyl-2-morpholinone (in the monohydrate form).

EXAMPLE 7

A solution of N-phosphonomethylglycine and sodium hydroxide is prepared as in Example 1, and 27.5 grams of the solution is added to ethyl glycidyl ether (5.1 grams, 0.05 mole). The solution is diluted with 30 ml. of water, and a drop of a phase-transfer catalyst solution is added. It is then rotated on a polymer wheel for 5 days, treated with 1.0 gram of ethyl glycidyl ether, rotated for another 10 days, warmed with charcoal and filtered to remove resinous material. The filtrate is rotoevaporated to dryness, and the solid is redried over potassium hydroxide pellets at 100° C. and <1 mm. Hg. An 8.0 gram portion of the product is dissolved in 30 ml. of water and passed through a column of ion exchange resin in the acid form. Cuts 8 through 18 (50 ml. each) are combined and passed through another column. The major cut is dried to yield 2.4 grams of 2-ethoxymethyl-4-phosphonomethyl-2-morpholinone (in the monohydrate form) as a cream colored friable glass. Elemental analysis gives 34.40% carbon, 6.67% hydrogen, 5.22% nitrogen and 12.17% phosphorus as against calculated values of 35.43%, 6.69%, 5.16% and 11.42% for $C_8H_{16}NO_6P \cdot H_2O$.

EXAMPLE 8

A solution of N-phosphonomethylglycine and sodium hydroxide is prepared as in Example 1, and 4.7 grams of isopropyl glycidyl ether is added to 18.6 grams of this solution. A drop of phase-transfer catalyst solution is added, and the mixture is rotated on a polymer wheel for almost 6 days. An oil layer is extracted with ethyl ether, separated and discarded. A 12 gram portion of the remaining light yellow aqueous layer is filtered with charcoal and passed through a column of ion exchange resin in the acid form. The product, dried several times to an off-white blown glass, is 6-isopropoxymethyl-4-phosphonomethyl-2-morpholinone (in the hemihydrate form). Elemental analysis gives 39.13% carbon, 6.93% hydrogen, 5.07% nitrogen and 11.21% phosphorus as against calculated values of 39.14%, 7.03%, 5.20% and 11.22% for $C_9H_{18}NO_6P \cdot \frac{1}{2} H_2O$.

EXAMPLE 9

A solution of N-phosphonomethylglycine and sodium hydroxide is prepared as in Example 1, and 2.7 grams of methyl glycidyl ether is added to 18.7 grams of this solution. The mixture is rotated on a polymer wheel for about 10 days. The solution is then extracted three times with ethyl ether, and residual ether is blown out with nitrogen. The remaining solution is passed through a column of ion exchange resin in the acid form and dried. The product, obtained as a friable glass, is 1.4 grams of 6-methoxymethyl-4-phosphonomethyl-2-morpholinone. Elemental analysis gives 35.49% carbon, 6.06% hydrogen, 5.43% nitrogen and 11.75% phosphorus as against calculated values of 35.15%, 5.90%, 5.86% and 12.95% for $C_7H_{14}NO_6P$.

EXAMPLE 10

A solution of N-phosphonomethylglycine and sodium hydroxide is prepared as in Example 1, and 3.4 grams of allyl glycidyl ether is added to 18.7 grams of this solution. The mixture is rotated on a polymer wheel for about 10 days, extracted twice with ethyl ether and blown with nitrogen. A 16.9 gram portion of the remaining colorless solution is passed through a column of ion exchange resin in the acid form. Cuts 24 through 50 are collected, dried and redried at 50° C. and <1 mm. Hg. The product, obtained as a cream colored friable glass, is 6-allyloxymethyl-4-phosphonomethyl-2-morpholinone. Elemental analysis gives 40.33% carbon, 6.43% hydrogen, 4.97% nitrogen and 10.99% phosphorus as against calculated values of 40.76%, 6.08%, 5.28% and 11.68% for $C_9H_{16}NO_6P$.

EXAMPLE 11

A reaction mixture is prepared from N-phosphonomethylglycine, sodium hydroxide and a small excess of ethylene oxide in water as described in Example 1, and this mixture is subjected to high-performance ion exchange chromatography on a modified sulfonic acid resin column, eluting with distilled water. Tubes 47 and 48 (20 ml. each) are chosen from the center of the major peak, combined and dried below 25° C. in a vacuum dessicator at 3 mm. Hg. The product is a brittle glass with a single carbonyl stretching frequency of 5.77μ (free carboxylic acid) in the infrared spectrum. Elemental analysis gives 27.35% carbon, 6.07% hydrogen, 6.37% nitrogen and 13.57% phosphorus as against calculated values of 27.04%, 5.90%, 6.31% and 13.94% for $C_5H_{12}NO_6P \cdot \frac{1}{2} H_2O$, N-(2-hydroxyethyl)-N-phosphonomethylglycine in the hemihydrate form. This free acid product is then heated overnight on a watch glass at 110° C. There is obtained a foamed colorless brittle glass lacking the 5.77μ absorption, but showing a new, stronger lactone carbonyl stretch at 5.69μ. Elemental analysis gives 30.66% carbon, 5.31% hydrogen, 7.09% nitrogen and 15.69% phosphorus as against calculated values of 30.78%, 5.17%, 7.18% and 15.87% for $C_5H_{10}NO_5P$, 4-phosphonomethyl-2-morpholinone.

The post-emergence herbicidal activity of various compounds of this invention is demonstrated as follows. The active ingredients are applied in spray form to 14–21 day-old specimens of various plant species. The spray, a water or organic solvent-water solution containing active ingredient and a surfactant (35 parts butylamine salt of dodecylbenzenesulfonic acid and 65 parts tall oil condensed with ethylene oxide in the ratio of 11 moles ethylene oxide to 1 mole tall oil), is applied to the plants in different sets of pans at several rates (kg per hectare) of active ingredient. The treated plants are placed in a greenhouse and the effects are observed and recorded after approximately 2 weeks or approximately 4 weeks. The data is given in Table I.

The post-emergence herbicidal activity index used in Table I is as follows:

| Plant Response | Index |
|---|---|
| 0–24% Injury | 0 |
| 25–49% Injury | 1 |
| 50–74% Injury | 2 |
| 75–99% Injury | 3 |
| All Killed | 4 |
| Species not present at time of treatment | * |

In said Table, the compounds are designated by the Example numbers, WAT indicates weeks after treatment, and the plant species treated are each represented by a code letter as follows:

A — Canada Thistle
B — Cocklebur
C — Velvet Leaf
D — Morning Glory
E — Lambsquarters
F — Smartweed
G — Nutsedge
H — Quackgrass
I — Johnson Grass
J — Downy Brome
K — Barnyard Grass

TABLE I

| Compound | WAT | kg/h | A | B | C | D | E | F | G | H | I | J | K |
|---|---|---|---|---|---|---|---|---|---|---|---|---|---|
| 1 | 2 | 4.48 | 0 | 0 | 0 | 1 | 1 | 0 | 0 | 0 | 0 | 0 | 0 |
| 2 | 2 | 11.2 | 1 | * | 1 | 2 | 3 | 0 | 1 | 0 | 1 | 1 | 2 |
|   | 4 | 11.2 | 1 | * | 2 | 2 | 3 | 1 | 2 | 2 | 2 | 0 | 2 |
| 3 | 2 | 11.2 | 2 | * | 2 | 2 | 4 | * | 1 | 1 | 1 | 3 | 3 |
|   | 4 | 11.2 | 2 | * | 3 | 3 | 4 | * | 1 | 2 | 0 | 3 | 3 |
| 4 | 2 | 11.2 | 1 | 1 | 1 | 1 | 1 | 1 | 0 | 1 | 0 | 0 | 1 |
|   | 4 | 11.2 | 1 | 1 | 1 | 1 | 1 | 1 | 0 | 1 | 0 | 0 | 1 |
| 5 | 2 | 11.2 | 1 | 1 | 0 | 1 | 2 | 1 | 0 | 0 | 0 | 1 | 2 |
|   | 4 | 11.2 | 2 | 1 | 0 | 1 | 2 | 2 | 1 | 1 | 1 | 2 | 2 |
| 6 | 2 | 11.2 | 1 | 2 | 1 | 1 | 1 | 1 | 2 | 1 | 1 | 1 | 2 |
|   | 4 | 11.2 | 2 | 2 | 1 | 1 | 1 | 0 | 2 | 1 | 0 | 1 | 2 |
| 7 | 2 | 11.2 | 4 | 3 | 2 | 2 | 3 | 3 | 3 | 3 | 3 | 2 | 3 |
|   | 4 | 11.2 | 4 | 4 | 2 | 2 | 4 | 4 | 3 | 4 | 3 | 2 | 4 |
|   | 2 | 5.6 | 2 | 2 | 1 | 1 | 2 | 2 | 2 | 1 | 2 | 1 | 3 |
|   | 4 | 5.6 | 2 | 3 | 1 | 1 | 3 | 2 | 3 | 2 | 2 | 1 | 3 |
| 8 | 2 | 11.2 | 1 | 3 | 2 | 1 | 3 | 4 | 1 | 1 | 1 | 2 | 3 |
|   | 4 | 11.2 | 1 | 3 | 2 | 1 | 4 | 4 | 1 | 1 | 1 | 2 | 4 |
|   | 2 | 5.6 | 0 | 2 | 1 | 1 | 1 | 3 | 1 | 1 | 1 | 0 | 2 |
|   | 4 | 5.6 | 1 | 2 | 1 | 1 | 1 | 3 | 1 | 1 | 1 | 1 | 2 |
| 9 | 2 | 11.2 | 1 | 1 | 1 | 1 | 2 | 2 | 1 | 1 | 1 | 0 | 1 |
|   | 4 | 11.2 | 2 | 2 | 2 | 2 | 4 | 4 | 0 | 0 | 0 | 0 | 2 |
|   | 2 | 5.6 | 1 | 1 | 1 | 1 | 1 | 1 | 1 | 1 | 0 | 0 | 1 |
|   | 4 | 5.6 | 1 | 2 | 1 | 2 | 1 | 4 | 1 | 0 | 0 | 2 | 1 |
| 10 | 2 | 11.2 | 0 | 1 | 1 | 1 | 0 | 0 | 0 | 0 | 1 | 0 | 1 |
|   | 4 | 11.2 | 0 | 1 | 1 | 1 | 1 | 0 | 0 | 0 | 0 | 0 | 1 |
|   | 2 | 5.6 | 1 | 0 | 0 | 1 | 1 | 0 | 0 | 0 | 0 | 0 | 1 |
|   | 4 | 5.6 | 0 | 0 | 0 | 0 | 1 | 0 | 0 | 0 | 1 | 0 | 0 |

The herbicidal compositions, including concentrates which require dilution prior to application to the plants, of this invention contain from 5 to 95 parts by weight of at least one active ingredient and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, all parts being by weight of the total composition. Where required from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these. From the viewpoint of economy and convenience, water is the preferred diluent.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhance so their efficacy. By the term "surface-active agent" it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isethionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acyl) taurates.

Water dispersible powder compositions can be made containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total composition. Where required, from about 0.1 to 2.0 parts by weight of the solid inert extender can be replaced by a corrosion inhibitor or anti-foaming agent or both.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface active agent and about 4 to 94 parts solvent, all parts being by weight based on the total weight of emulsifiable oil.

Although compositions of this invention can also contain other additaments, for example, fertilizers, phytotoxicant and plant growth regulants, pesticides and the like used as adjuvants or in combination with any of the above-described adjuvants, it is preferred to employ the compositions of this invention alone with sequential treatments with the other phytotoxicants, fertilizers and the like for maximum effect. For example, the field could be sprayed with a composition of this invention either before or after being treated with fertilizers, other phytotoxicants and the like. The compositions of this invention can also be admixed with the other materials, e.g., fertilizers, other phytotoxicants, etc., and applied in a single application. Chemicals useful in combination with the active ingredients of this invention either simultaneously or sequentially include, for example, triazines, ureas, carbamates, acetamides, acetanilides, uracils, acetic acids, phenols, thiolcarbamates, triazoles, benzoic acids, nitriles and the like.

Fertilizers useful in combination with the active ingredients include, for example, ammonium nitrate, urea, potash, and superphosphate.

When operating in accordance with the present invention effective amounts of the lactones are applied to above-ground portions of plants. The application of liquid and particulate solid herbicidal compositions to above-ground portions of plants can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by spraying the compositions on the aquatic plants in the area where control of the aquatic plants is desired.

The application of an effective amount of the compounds of this invention to the plant is essential and critical for the practice of the present invention. The exact amount of active ingredient to be employed is dependent upon the response desired in the plant as well as such other factors as the plant species and stage of development thereof, and the amount of rainfall as well as the specific lactone employed. In foliar treatment for the control of vegetative growth, the active ingredients are applied in amounts from about 0.56 to about 22.4 or more kilograms per hectare. In applications for the control of aquatic plants, the active ingredients are applied in amounts of from about 0.1 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although the invention is described with respect to specific modifications, the details thereof are not to be construed as limitations except to the extent indicated in the following claims.

What is claimed is:

1. A compound of the formula

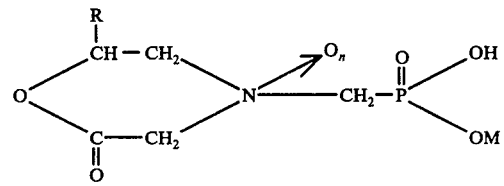

wherein $n$ is zero or one, M is hydrogen or alkali metal, and R is hydrogen, methyl, ethyl, hydroxymethyl, lower alkoxymethyl or lower alkenoxymethyl.

2. A compound as defined in claim 1 wherein $n$ is one.

3. A compound as defined in claim 1 wherein $n$ is zero and M is alkali metal.

4. A compound as defined in claim 3 wherein R is hydrogen.

5. A compound as defined in claim 3 wherein R is methyl.

6. A compound as defined in claim 1 wherein $n$ is zero and M is hydrogen.

7. A compound as defined in claim 6 wherein R is lower alkoxymethyl.

8. A compound as defined in claim 7 wherein R is ethoxymethyl.

9. A compound as defined in claim 7 wherein R is isopropoxymethyl.

10. A compound as defined in claim 7 wherein R is methoxymethyl.

11. A herbicidal composition comprising an inert adjuvant and a herbicidally effective amount of a compound of claim 1.

12. A herbicidal composition comprising an inert adjuvant and a herbicidally effective amount of a compound of claim 2.

13. A herbicidal composition cimprising an inert adjuvant and a herbicidally effective amount of a compound of claim 3.

14. A herbicidal composition cimprising an inert adjuvant and a herbicidally effective amount of a compound of claim 4.

15. A herbicidal composition comprising an inert adjuvant and a herbicidally effective amount of a compound of claim 5.

16. A herbicidal composition comprising an inert adjuvant and a herbicidally effective amount of a compound of claim 6.

17. A herbicidal composition comprising an inert adjuvant and a herbicidally effective amount of a compound of claim 7.

18. A herbicidal composition comprising an inert adjuvant and a herbicidally effective amount of a compound of claim 8.

19. A herbicidal composition comprising an inert adjuvant and a herbicidally effective amount of a compound of claim 9.

20. A herbicidal composition comprising an inert adjuvant and a herbicidally effective amount of a compound of claim 10.

21. A herbicidal method which comprises contacting a plant with a herbicidally effective amount of a compound of claim 1.

22. A herbicidal method which comprises contacting a plant with a herbicidally effective amount of a compound of claim 2.

23. A herbicidal method which comprises contacting a plant with a herbicidally effective amount of a compound of claim 3.

24. A herbicidal method which comprises contacting a plant with a herbicidally effective amount of a compound of claim 4.

25. A herbicidal method which comprises contacting a plant with a herbicidally effective amount of a compound of claim 5.

26. A herbicidal method which comprises contacting a plant with a herbicidally effective amount of a compound of claim 6.

27. A herbicidal method which comprises contacting a plant with a herbicidally effective amount of a compound of claim 7.

28. A herbicidal method which comprises contacting a plant with a herbicidally effective amount of a compound of claim 8.

29. A herbicidal method which comprises contacting a plant with a herbicidally effective amount of a compound of claim 9.

30. A herbicidal method which comprises contacting a plant with a herbicidally effective amount of a compound of claim 10.

* * * * *